United States Patent [19]

Komoda et al.

[11] Patent Number: 5,023,079

[45] Date of Patent: Jun. 11, 1991

[54] HEPTAENE V-28-3 ANTIBIOTIC DERIVATIVE

[75] Inventors: Yasuo Komoda, Tokyo; Yasunori Yokogawa; Masahiko Okunishi, both of Kanagawa; Koichi Ishii; Hiroshiro Shibai, both of Kanagawa; Ryosaku Noumi, Hiroshima, all of Japan

[73] Assignee: Ajinomoto Co., Inc., Tokyo, Japan

[21] Appl. No.: 403,033

[22] Filed: Sep. 1, 1989

Related U.S. Application Data

[63] Continuation-in-part of Ser. No. 164,973, Mar. 7, 1988, abandoned.

[30] Foreign Application Priority Data

Mar. 6, 1987 [JP] Japan .................................. 62-051570

[51] Int. Cl.$^5$ ............................................. A61K 35/74

[52] U.S. Cl. .................................... 424/120; 424/123; 424/124

[58] Field of Search ...................... 424/120, 123, 124

[56] References Cited

PUBLICATIONS

Chemical Abstracts 106:137002d (1987).

*Primary Examiner*—Jerome D. Goldberg
*Attorney, Agent, or Firm*—Oblon, Spivak, McClelland, Maier & Neustadt, P.C.

[57] ABSTRACT

An antimycotic agent having a high degree of antimicrobial activity towards *Eumycetes* and with a level of toxicity lower than that of heptaene antibiotic V-28-3 is disclosed. This compound is a methyl ester derivative of heptaene antibiotic V-28-3.

4 Claims, 4 Drawing Sheets

HEPTAENE V-28-3 ANTIBIOTIC DERIVATIVE

This application is a Continuation-In-Part of application Ser. No. 164,973, filed on Mar. 7, 1988, now abandoned.

BACKGROUND OF THE INVENTION

1. Field of the Invention

This invention relates to antibiotics.

2. Discussion of the Background

Recently, the treatment of bacteriosis has been greatly improved by the use of antibiotics and many other chemotherapeutic agents. The use of these chemotherapeutic agents, however, has posed a difficult problem, i.e., profunda mycosis caused by the infection of Eumycetes.

The inventors have already discovered a new heptaene antibiotic (V-28-3) which exhibits antimycotic activity, and filed in Japan a patent application on this compound (Japanese Patent First Publication No. 61-189224). Whereas this substance exhibits intense antimycotic activity, it is highly zootoxic, so that it requires further improvement before it can be used as an antibiotic.

There is accordingly a need for a compound possessing the advantageous properties of this new heptaene compound but not its disadvantages. There is a need for a new antimycotic agent which has higher antimicrobial activity and less toxicity.

SUMMARY OF THE INVENTION

Accordingly, it is an object of this invention to provide a new heptaene derivative having a high degree of antimicrobial activity towards Eumycetes.

It is another object of this invention to provide a novel heptaene derivative having a lower zooblast toxicity than that of heptaene V-28-3.

The inventors have now discovered a novel heptaene derivative which satisfies all of these objects, and other objects which will become apparent from a reading of the description of the invention given hereinbelow. This novel heptaene derivative is a methyl esterified heptaene V-28-3. The present invention also relates to a process for producing this novel methyl esterified heptaene and to a method for the treatment of bacteriosis in a patient suffering therefrom.

BRIEF DESCRIPTION OF THE FIGURES

A more complete appreciation of the invention and many of its attendant advantages will be readily obtained as the same becomes better understood by reference to the following detailed description when considered in connection with the accompanying figures, wherein.

DETAILED DESCRIPTION OF THE PREFERRED EMBODIMENTS

The inventors have synthesized derivatives of heptaene antibiotic V-28-3 for the purpose of obtaining an antimycotic agent with a high degree of antimicrobial activity towards Eumycetes and with a lower level of toxicity. As a result, the inventors discovered that methyl esterified V-28-3 (V-28-3M) was a new heptaene derivative with a higher degree of antimicrobial activity towards Eumycetes and a lower zooblast toxicity than those of V-28-3, and thereby completed this invention.

V-28-3M can be produced by subjecting V-28-3 to a usual methyl esterification reaction. For example V28-3M can be produced by adding a diazomethane solution prepared by the usual method to a methyl alcohol suspension of V-28-3 at ice temperature, and then stirring the solution at room temperature for about 30 minutes. Obviously other conventional methyl esterification reactions may be used to methyl esterify V-28-3, if desired. These reactions are well known tho those skilled in the art of chemical synthesis.

The starting material V-28-3 can be produced according to a method described in the official report for Japanese Patent first Publication 61-189224. The disclosure of Japanese Patent First Publication 61-189224 is summarized below.

Heptaene antibiotic V-28-3 has following physicochemical properties: (a) Appearance: yellow crystals; (b) Elementary analysis: C(59.39%), H(7.38%), N(2.46%); (c) Mol. wt.:1113 (measured by MS); (d) Mol. formula: $C_{58}H_{84}N_2O_{19}$. (e) Optical rotation: $[\alpha]^{26}_D + 335°$ (0.1%, DMSO); (f) M.pt.: Browned at 170 deg.C.; (g) Solubility in solvents: Insol. in water, ethyl ether, hexane and chloroform; slightly soluble in methanol, ethanol, and n-butanol; soluble in DMSO and DMF; (h) Color reaction: Positive to phenol-sulphuric acid; negative to ferric chloride; positive to ninhydrin; positive to conc. sulphuric acid; positive to iodine.

V-28-3 can be produced by Streptomyces arenae V-28-3 (FERM-P 8099, FERM BP-1537), which is incubated in a nutrient medium at 20-35 deg.C. for 24-36 hrs. After the incubation, the antibiotic is isolated from the grown cells or from the medium in a conventional manner (e.g., centrifugation, filtration) and is purified.

The V-28-3M produced by esterification of V-28-3 can be isolated using any method generally used for antibiotics isolation. For example, V-28-3M can be isolated after concentrating the reaction liquid under reduced pressure.

The V-28-3M thus obtained gives a single peak at t=7.5 minutes on high performance liquid chromatography (hereinafter referred to as HPLC, 1.0 ml/minute flow rate) using a Novapack C18 carrier (Waters), a 10 mM ammonium acetate buffer solution containing 65% acetonitrile as a mobile phase, and a UV (405 nm and 254 nm) detector.

V-28-3M had the following physicochemical properties.

Figure 1:
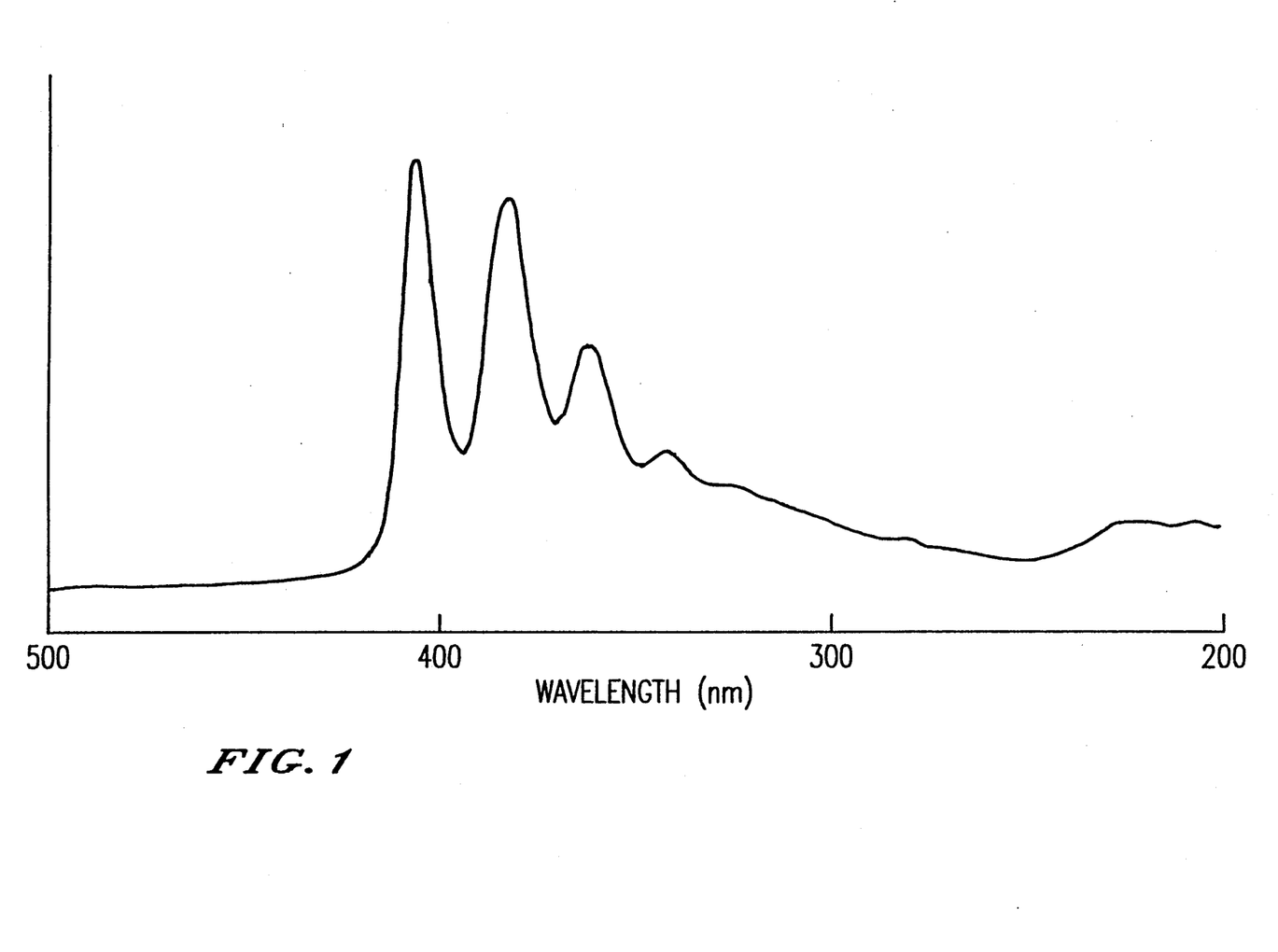
FIG. 1 provide the UV spectrum of the methyl esterified heptaene of the present invention, V-28-3M, as measured in methyl alcohol.

1) Elementary analysis (%): C: 58.95, H: 7.64, N: 2.39
2) Molecular weight (FABMS, (M+H)+):1127
3) Specific rotation : $[\alpha]_D^{20} + 296°$ (C=0.1% DMSO)
4) Melting point : It turns brown at 135° C.
5) UV spectrum : As shown in FIG. 1
6) Solubility in solvents : insoluble in water, diethyl ether, hexane and chloroform; slightly soluble in methanol, ethanol and n-butanol; soluble in dimethyl sulfoxide and N,N-dimethylformamide.

Figure 2:
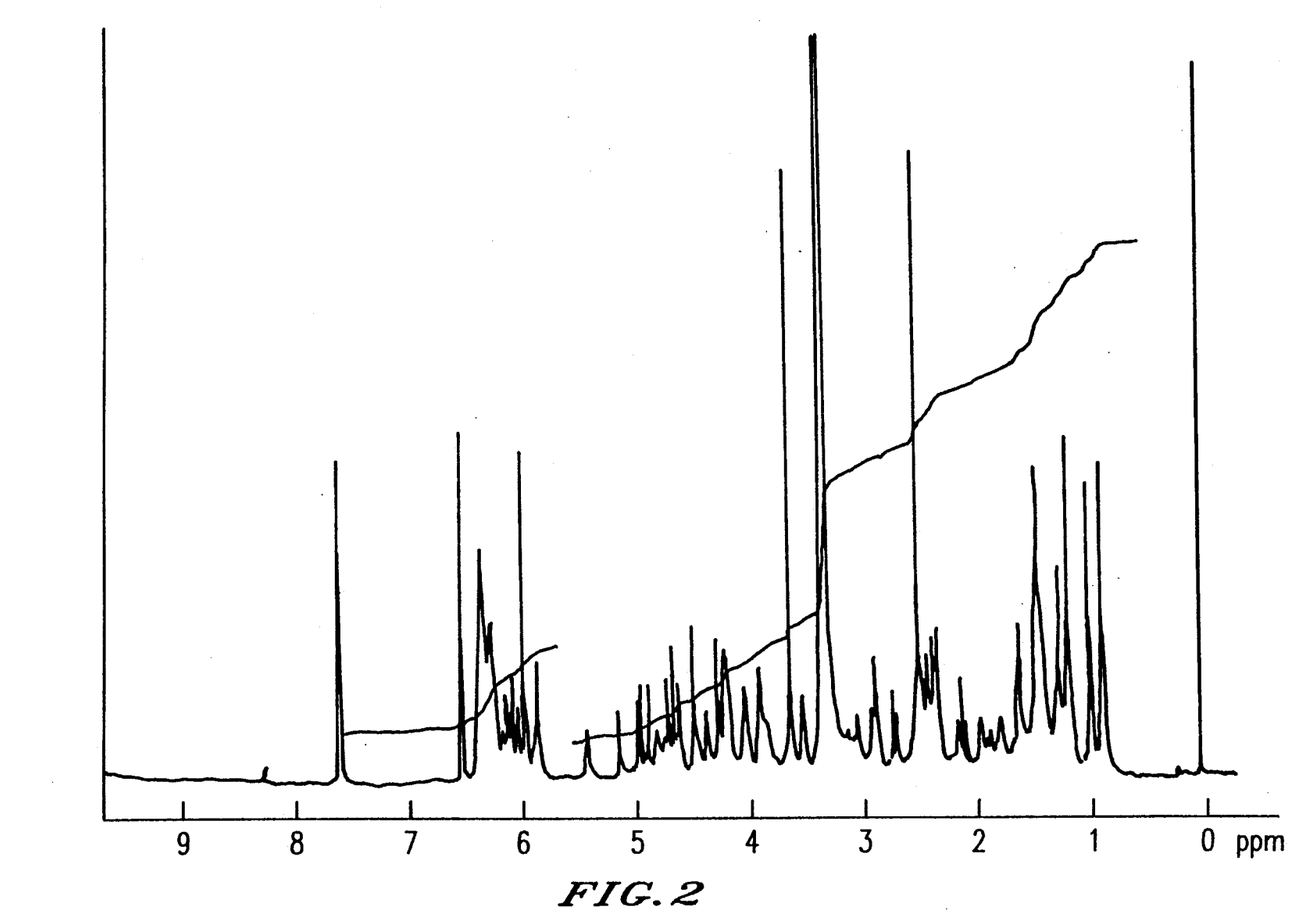
FIG. 2 provides a $^1$H-NMR spectra of V-28-3M measured at 400-MHz.
Figure 3:
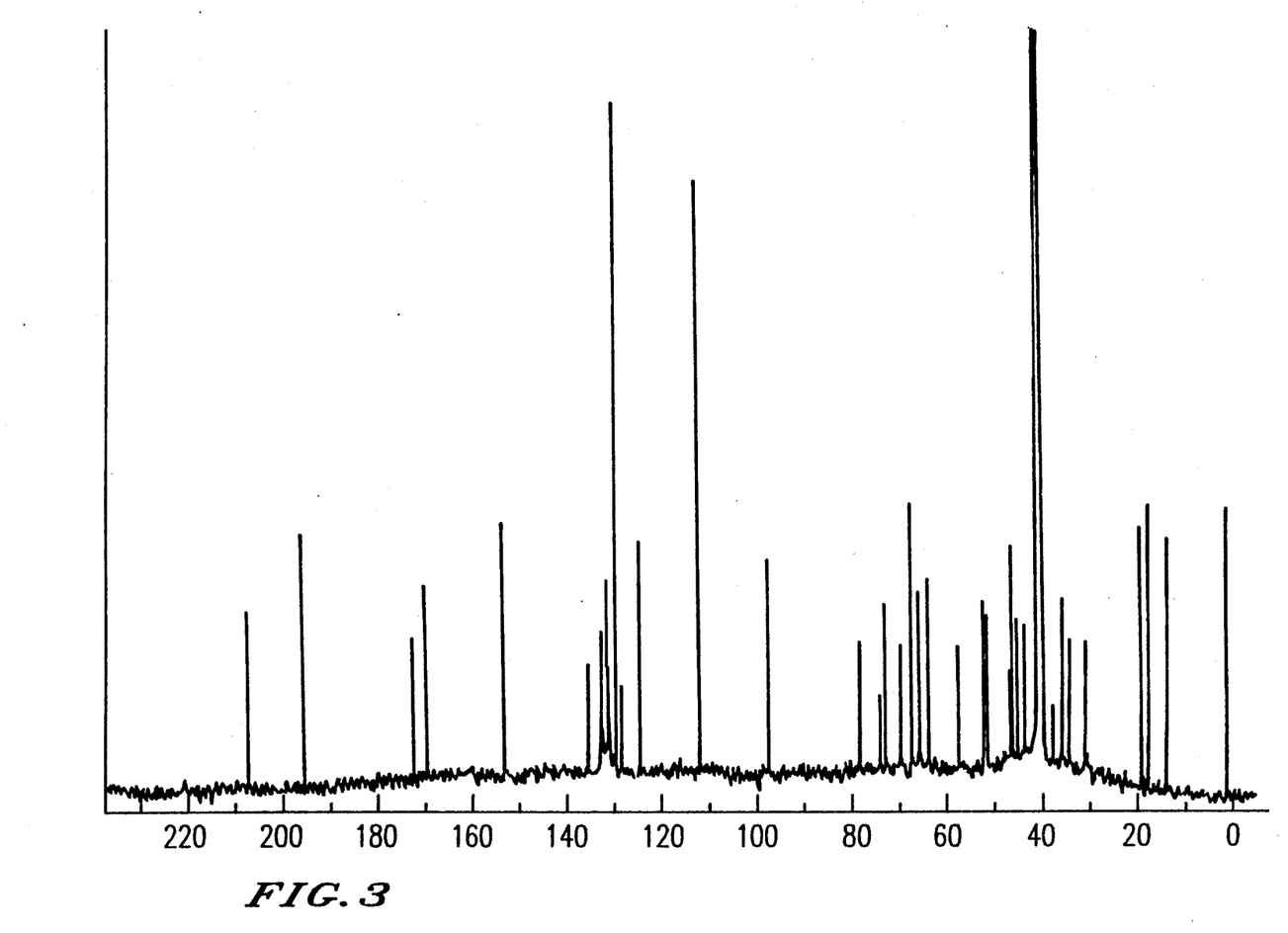
FIG. 3 provides a $^{13}$C-NMR spectra of V-28-3M as measured at 100 MHz.
Figure 4:
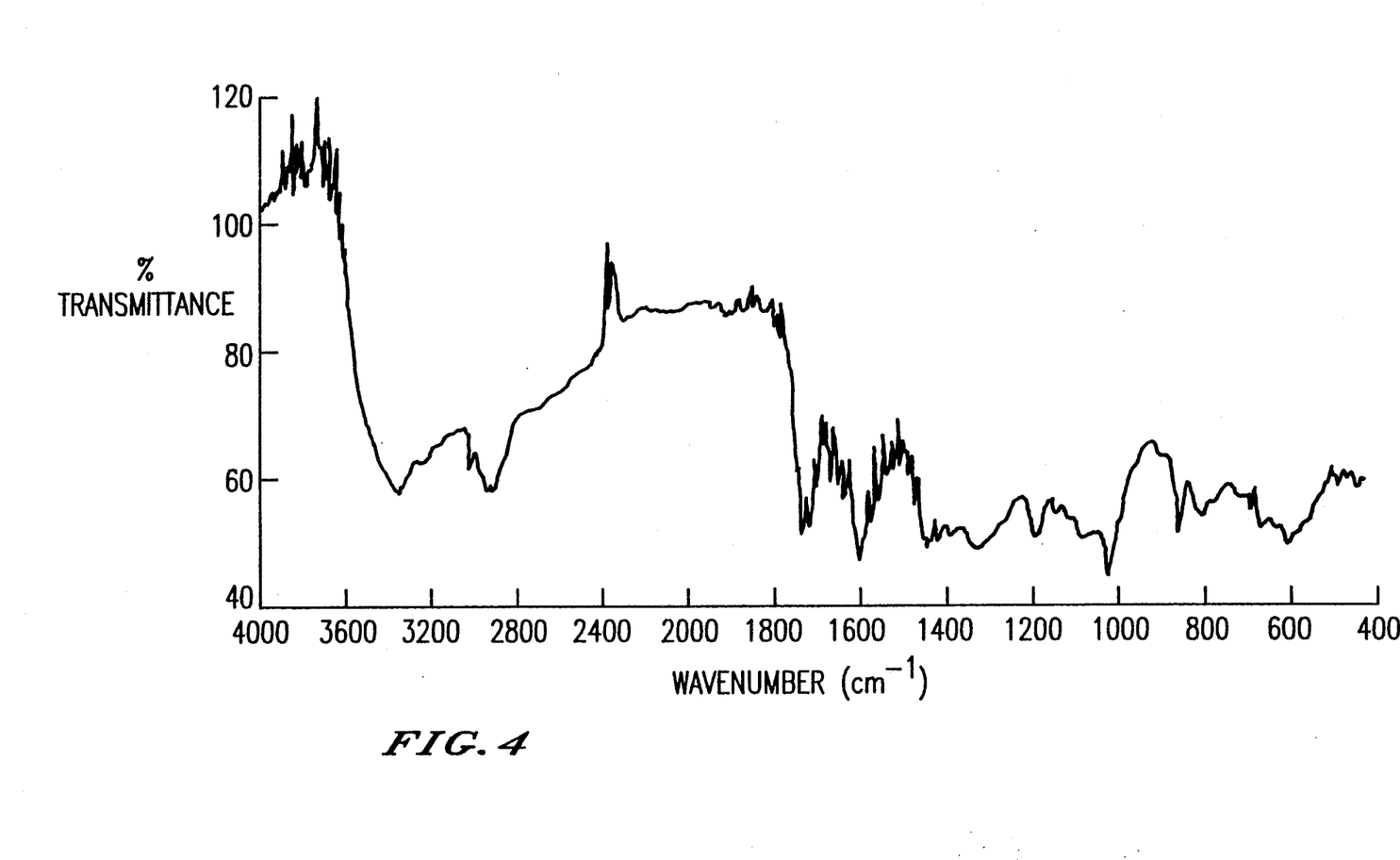
FIG. 4 provides a IR spectra of V-28-3M as measured in KBr.

7) Color reaction : Phenol-sulfuric acid : positive, ferric chloride: negative, ninhydrin : positive, concentrated sulfuric acid : positive, iodine : positive.
8) $^1$H-NMR spectrum : As shown in FIG. 2
9) $^{13}$C-NMR spectrum : As shown in FIG. 3
10) UV λ MeOH (ε): 405 (85,510), 382 (77,551) max 362 (46,531), 344 (25,714)
11) IR spectrum (KRr):P As shown in FIG. 4.

Melting point and specific rotation values are dependent on the purity of a sample. Accordingly, melting point temperatures which vary ±3° C. and specific rotation values which vary ±3° are considered to represent V-28-3M and fall within the scope of the present invention. Compounds having melting points and specific rotations within these ranges are likewise considered to be within the scope of the present invention.

As shown in Table 1, the minimal inhibitory concentration (MIC) of V-28-3M towards *Candida albicans* ATCC 10231 is lower than the MIC of amphotericin B and V-28-3, and V-28-3M displayed strong antimicrobial activity.

TABLE 1

| | Minimal inhibitory concentration (MIC, μg/ml) | | |
|---|---|---|---|
| Strain name | V-28-3M | V-28-3 | amphotericin B |
| Candida albicans (ATCC 102331) | 0.39 | 0.78 | 1.56 |

The experiment (Table 1) was made by the usual MIC measuring method using Sabraud's agar. The MIC was determined 48 hours later.

The cytotoxicity (50% growth inhibitory concentration) of V-28-3M towards L1210 cells, as listed in Table 2, is about 6 times higher than that of V-28-3.

TABLE 2

| Cytotoxicity (50% growth inhibitory concentration, (μg/ml)) | | |
|---|---|---|
| Cell name | V-28-3M | V-28-3 |
| L1210 | 1.4 | 0.23 |

RPMI1640 culture medium was used for the experiment (Table 2), which was conducted by the usual cell growth inhibitory measuring method. Cytotoxicity was determined 48 hours later. Effect of V-28-3M on experimental candidiasis Male ICR-strain mice, weighing 20–22 g, were used in groups of 10. A 0.2 ml cell suspension of *Candida albicans* (strain C3) was injected IV via the tail vein, inoculum size being $2.5 \times 10^7$ cells/mouse. The test drugs (0.2 ml) were administered IV via the tail vein once at 1 hr after the infection.

The therapeutic effect of the test drugs was expressed as the survival ratio at day-8 after infection.

Results

The therapeutic effect of V-28-3M was comparable to amphotericin B as shown in Table 3.

TABLE 3

| Effect of V-28-3M on mouse candidiasis | | |
|---|---|---|
| Drugs | Dose (mg/kg) | Survival ratio (%) |
| V-28-3M | 0.5 | 90 |
| | 0.25 | 90 |
| | 0.125 | 10 |
| Amphotericin B | 0.5 | 100 |
| | 0.25 | 70 |

TABLE 3-continued

| Effect of V-28-3M on mouse candidiasis | | |
|---|---|---|
| Drugs | Dose (mg/kg) | Survival ratio (%) |
| | 0.125 | 0 |
| saline | — | 0 |

Acute toxicity (LD$_{50}$, IV)

An acute toxicity study was carried out with male ICR-strain mice. LD$_{50}$ (50% lethal dose) was calculated on the basis of the number of survivors at day-5 after IV administration of the drugs.

Results

LD$_{50}$ of V-28-3M was more than 50 mg/kg, whereas amphotericin B was 4.1 mg/kg as shown in Table 4.

TABLE 4

| | LD$_{50}$ (mg/kg) |
|---|---|
| Drugs | LD$_{50}$ (mg/kg) |
| V-28-3M | >50* |
| Amphotericin B | 4.1 |

*All of mice tested survived with 50 mg/kg.--;

As shown in Table 1, V-28-3M displays strong antimicrobial activity towards *Candida albicans*. And as shown in Table 2, it has a low level of toxicity and can be used as a new antimycotic agent.

The effectiveness of V-28-3M in treating candidiasis has been established as shown in Table 3 and its toxicity is substantially lower than amphotericin B as shown in Table 4.

V-28-3M may be formulated as a pharmaceutical into conventional forms as solutions and as solid preparations. Preferred pharmaceutical compositions are pharmaceutical compositions used for preparation of amphotericin B pharmaceutical compositions. Such compositions are well known to those skilled in the art.

The pharmaceutical preparations containing V-28-3M may be used at dosage ranges from about 0.05 mg/kg to about 10 mg/kg and preferably from about 0.1 mg/kg to about 5 mg/kg. However, dosage ranges above or below these preferred ranges are possible and may be desirable for treating specific patients and specific infections. The dosage and administration of the pharmaceutical compositions of the present invention may be determined on a patient-by-patient basis and adjusted during treatment to achieve an optical level of administration for the particular infection. The adjustment of pharmaceutical dosages is standard procedure in the medical treatment of infections.

The pharmaceutical compositions containing V-28-3M may be administered orally, topically or by mans of injection, with administration by injection being the preferred method of administering the pharmaceutical compositions.

Other features of the invention will become apparent in the course of the following descriptions of exemplary embodiments which are given for illustration of the invention and are not intended to be limiting thereof.

EXAMPLE

A 100 ml culture medium of the composition set out in Table 3 was poured into a 500 ml capacity flask, and sterilized by heating at 120° C. for 10 minutes.

TABLE 3

| Composition of culture medium* | |
|---|---|
| Components | Content (in 1.0 liter) |
| Soluble starch | 30.0 g |
| Malt extract | 6.0 g |
| Yeast extract | 6.0 g |
| Polypeptone | 12.0 g |
| Table salt | 5.0 g |
| $MgSO_4.7H_2O$ | 0.5 g |

*(pH: 7.0)

Using a platinum loop, this medium was inoculated with *Streptomyces arenae* V-28-3 (FERM P-8099) grown on an agar slant of the same composition, and cultured at 27° C. for 3 days while being agitated.

This strain identified above by FERM P-8099 was originally deposited on Feb. 16, 1985 at the Fermentation Research Institute, Agency of Industrial and Technology, Ministry of International Trade and Industry (FRI), 1-3, Higashi 1-chome, Tsukuba-shi, Ibaragi-ken 305, Japan, and was accorded the FERM P-8099 indicated above. This strain deposit was then converted into a deposit under the Budapest Treaty on Oct. 27, 1987, and was accorded the corresponding FERM BP-1537.

Meanwhile, a 20 liter culture medium (silicon KM-75 10 ml as an antifoamer was further added to the solution of the same composition) was placed in a 30 liter capacity jar fermenter, and sterilized by heating at 120° C. for 10 minutes. Then, the solution was inoculated with the above culture medium, and aerobic culture stirring was performed at 27° C. for 24 hours (aeration amount ½ V.V.M.; stirring revolution 200 rpm.) The culture solution was centrifuged (4,000 rpm, for 10 minutes), and a 1.6 kg microbial cake was obtained. 1.5 liter of 80% methanol was added to a 500 g cell cake of the 1.6 kg cake, and ammonia water was added to adjust the pH to 9.5.

Then, the mixture was stirred slowly, and the extraction operation was continued for 3 hours at room temperature. The solution was centrifuged to remove insoluble matter and to obtain the extract. The pH of the extract solution was lowered to 7.0 and 1.5 liters of water was added.

The solution was then made to pass through a DI-AION HP-20 (manufactured by Mitsubishi Chemical Industries, adsorption carrier) column (10×30 cm). After washing this column with a small quantity of 50% methanol, elution fractions were eluted with 80% methanol containing 0.45% ammonia water.

A fraction which has antimicrobial activity towards *Candida albicans* HUT 7501 was collected from the elution fractions and concentrated under reduced pressure to obtain a yellowish brown precipitate by centrifugation. By washing this precipitate with cold acetone and drying it under reduced pressure, 600 mg of yellowish green powder was obtained.

This powder was suspended in 100 ml chloroform solution, and was made to pass through a Hyflo-Super-Cel column (5×20 cm). After washing the column with 100 ml chloroform and then with a 100 ml chloroform-methanol mixture (1:1 mixing ratio) elution fractions were eluted with acetonitrile-0.05M ammonium acetate (pH 9.5) eluent (1:1 mixing ratio).

An active fraction was collected from the elution fractions, and the solvent was removed under reduced pressure. The produced precipitate was collected by centrifugation, washed with acetone, and dried under reduced pressure. Thus, 420 mg of yellow powder was obtained. 60 mg of the powder was dissolved in a 5.0 ml 66% tetrahydrofuran solution. This solution was made to pass through a LRP-1 column (Whatmann C-18 reversed phase chromatography carrier), and active antimicrobial fractions were eluted with an eluent of composition acetonitrile-0.05N ammonium acetate (pH 9.0) (4.5:5.5 mixing ratio).

The antimicrobial substance was separated to be eluted in two fractions. (The active substance eluted first was identified as Partricin B from its $^1$H-NMR spectrum). The antimicrobial active fraction eluted later was collected, and the solvent was slowly removed under reduced pressure conditions until a whitish turbidity was observed. The fraction was preserved at 5° C. overnight to precipitate yellow crystals. The yellow crystals were collected by centrifugation, and washed with cold water and cold acetone, and then dried under reduced pressure. In this way 30 mg of V-28-3 was obtained.

The V-28-3 (20 mg) thus obtained was suspended in 4 ml methyl alcohol to which a tetrahydrofuran solution of diazomethane was added with the mixture as an ice-cold suspension. After stirring the reactant liquid at room temperature for 30 minutes, nitrogen gas was blown over the reactant liquid to remove the solvent. 21 mg of dry solid matter was obtained.

The dry solid matter was dissolved in the lower layer liquid of a chloroform-methyl alcohol-water mixture liquid (2:2:1 mixing ratio). This was made to undergo countercurrent droplet distribution chromatography with the lower layer liquid as a solid phase and the upper layer liquid as a mobile phase.

By means of the HPLC mentioned before, the eluate was examined, and fractions containing only V-28-3M were concentrated and dried. As a result, V-28-3M (15 mg) was separated as a yellow powder. The results of an elementary analysis of the yellow powder are: C=58.95%, H=7.64%, and N=2.39%. UV spectrum, $^1$H-NMR spectrum and $^{13}$C-NMR spectrum are shown in FIGS. 1, 2 and 3, respectively. The IR spectrum of V-28-3M is shown in FIG. 4.

FIG. 1 presents the UV spectrum of V-28-3M measured in methyl alcohol, showing the intensity of absorption on the longitudinal axis and wavelength (nm) on the transverse axis. FIGS. 2 and 3 give $^1$H-NMR and $^{13}$C-NMR spectra, measured at 400 NHz and 100 MHz, respectively. The longitudinal axis shows the intensity of absorption and the transverse axis a chemical shift expressed in ppm based on TMS. FIG. 4 gives the IR spectrum obtained in KBr.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A compound having the following physicochemical properties:
   1) appearance: yellow powder;
   2) molecular weight (FABMS, $(M+H)^{30}$)=1127;
   3) molecular formula: $C_{59}H_{86}N_2O_{19}$;
   4) melting point: turns brown at 135° C.;
   5) UV spectrum: as shown in FIG. 1;
   6) solubility in solvents: insoluble in water, diethyl ether, hexane and chloroform; slightly soluble in methanol, ethanol and n-butanol; soluble in dimethyl sulfoxide and N,N-dimethylformamide;
7) color reaction: phenol-sulfuric acid: positive, ferric chloride: negative, ninhydrin: positive, concentrated sulfuric acid: positive, iodine: positive;
8) $^1$H—NMR spectrum: as shown in FIG. 2;
9) $^{13}$D—NMR spectrum: as shown in FIG. 3;
10) specific rotation: $[\alpha]_D^{20} + 296°$ (C=0.1% DMSO);
11) IR spectrum: as shown in FIG. 4.

2. A method for treating a patient in need of a treatment of bacteriosis, and said treatment comprising administering an amount effective to treat bacteriosis in said patient of a compound having the following physicochemical properties:
1) appearance: yellow powder;
2) molecular weight (FABMS, (M+H)$^{30}$)=1127;
3) molecular formula: $C_{59}H_{86}N_2O_{19}$;
4) melting point: product turns brown at 135° C.;
5) UV spectrum: as shown in FIG. 1;
6) solubility: insoluble in water, diethyl ether, hexane and chloroform; slightly soluble in methanol, ethanol and n-butanol; and soluble in dimethyl sulfoxide and N,N-dimethylformamide;
7) color reaction: phenol-sulfuric acid: positive, ferric chloride: negative, ninhydrin: positive, concentrated sulfuric acid: positive, iodine: positive;
8) $^1$H—NMR spectrum: as shown in FIG. 2;
9) $^{13}$C—NMR spectrum: as shown in FIG. 3;
10) specific rotation: $[\alpha]_D^{20} + 296°$ (C=0.1% DMSO);
11) IR spectrum: as shown in FIG. 4

3. A method for producing a compound having the following physicochemical properties:
1) appearance: yellow powder;
2) molecular weight (FABMS, (M+H)$^{30}$)=1127;
3) molecular formula: $C_{59}H_{86}N_2O_{19}$;
4) melting point: product turns brown at 135° C.;
5) UV spectrum: as shown in FIG. 1;
6) solubility: insoluble in water, diethyl ether, hexane and chloroform; slightly soluble in methanol, ethanol and n-butanol; and soluble in dimethyl sulfoxide and N,N-dimethylformamide;
7) color reaction: phenol-sulfuric acid: positive, ferric chloride: negative, ninyydrin: positive, concentrated sulfuric acid: positive, iodine: positive;
8) $^1$H—NMR spectrum: as shown in FIG. 2;
9) $^{13}$C—NMR spectrum: as shown in FIG. 3;
10) specific rotation: $[\alpha]_D^{20} + 296°$ (C=0.1% DMSO);
11) IR spectrum: as shown in fIG. 4, said process comprising:
methyl esterifying heptaene V-28-3 by adding to a methyl alcohol suspension of V-28-3, at ice temperature, an amount of a diazomethane solution in tetrahydrofuran, sufficient to produce said compound, mixing for a period of time sufficient to produce said compound at room temperature, and recovering said compound.

4. The process of claim 3, wherein said recovering step comprises removing the methyl alcohol and tetrahydrofuran to obtain a dry product, and then isolating said compound from said dry product by chromatography.

* * * * *

UNITED STATES PATENT AND TRADEMARK OFFICE
CERTIFICATE OF CORRECTION

PATENT NO.   :  5,023,079               Page 1 of 2

DATED        :  JUNE 11, 1991

INVENTOR(S)  :  YASUO KOMODA ET AL

It is certified that error appears in the above-identified patent and that said Letters Patent is hereby corrected as shown below:

Column 1, line 59, delete "provide", insert --provides--;
        line 61, delete ".", insert --;--;
        line 67, after "provides", delete "a", insert --an--.

Column 2, line 14, delete "V28-", insert --V-28- --;
        line 21, delete "tho", insert --to--;
        line 32, after "$C_{58}H_{84}N_2O_{19}$", delete "." insert --;--;
        line 34, delete "deg.C", insert --°C--;
        line 42, delete "deg.C", insert --°C--.

Column 3, line 10, delete "(KRr):P", insert --(KBr)--;
        line 39, after "concentration", insert --)--; and
           after "(μg/ml)", delete second ")";
        line 46, delete "Effect of V-28-3M on experimental
           candidiasis.", insert --<u>Effect of V-28-3M on
           experimental candidiasis</u>.--

Column 4, line 55, delete "mans", insert --means--.

Column 5, line 1, delete title "TABLE 3", insert --TABLE 5--;
        line 42, delete "was", insert --were--.

UNITED STATES PATENT AND TRADEMARK OFFICE
CERTIFICATE OF CORRECTION

PATENT NO. : 5,023,079
DATED : June 11, 1991
INVENTOR(S) : Yasuo Komoda et al

It is certified that error appears in the above-indentified patent and that said Letters Patent is hereby corrected as shown below:

Column 6, line 63, delete "$(M+H)^{30})$", insert --$(M+H)^{+})$--.

Column 7, line 17, delete "$(M+H)^{30})$", insert --$(M+H)^{+})$--.

Column 8, line 4, delete "$(M+H)^{30})$", insert --$(M+H)^{+})$--.

Signed and Sealed this

Fourteenth Day of September, 1993

Attest:

BRUCE LEHMAN

*Attesting Officer*     *Commissioner of Patents and Trademarks*